United States Patent
Kuboi et al.

(10) Patent No.: US 11,116,388 B2
(45) Date of Patent: Sep. 14, 2021

(54) SHAPE MEASURING CYLINDRICAL FLEXIBLE BODY APPARATUS

(71) Applicant: OLYMPUS CORPORATION, Tokyo (JP)

(72) Inventors: Toru Kuboi, Machida (JP); Masaya Takahashi, Hachioji (JP); Tetsuya Morishima, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 455 days.

(21) Appl. No.: 16/033,262

(22) Filed: Jul. 12, 2018

(65) Prior Publication Data

US 2018/0317751 A1  Nov. 8, 2018

Related U.S. Application Data

(63) Continuation of application No. PCT/JP2016/051027, filed on Jan. 14, 2016.

(51) Int. Cl.
*A61B 1/00* (2006.01)
*A61B 1/005* (2006.01)
(Continued)

(52) U.S. Cl.
CPC ...... *A61B 1/00165* (2013.01); *A61B 1/00004* (2013.01); *A61B 1/00006* (2013.01);
(Continued)

(58) Field of Classification Search
CPC ............ A61B 1/00004; A61B 1/00165; A61B 2034/2061
See application file for complete search history.

(56) References Cited

U.S. PATENT DOCUMENTS

2002/0183592 A1* 12/2002 Suzuki ................. A61B 1/0055
                                                       600/145
2017/0020612 A1*  1/2017 Kuboi ................ A61B 1/00006
2018/0160882 A1*  6/2018 Kuboi .................... G01B 11/24

FOREIGN PATENT DOCUMENTS

JP    2001-169998 A    6/2001
JP    2007/044402 A    2/2007
(Continued)

OTHER PUBLICATIONS

International Search Report dated Apr. 12, 2016 issued in PCT/JP2016/051027.
(Continued)

*Primary Examiner* — Aaron B Fairchild
(74) *Attorney, Agent, or Firm* — Scully, Scott, Murphy & Presser, P.C.

(57) ABSTRACT

A shape measuring apparatus includes a cylindrical flexible body and a bend detection sensor. The sensor includes an optical fiber extending along the flexible body, a detection target to vary characteristics of detection light guided through the optical fiber in accordance with a curvature of the optical fiber, and a light detection unit to detect the detection light. The shape measuring apparatus also includes a shape calculating device to calculate a bend shape of the flexible body, based on the variation of the characteristics of the detection light, a cylindrical sheathing member sheathing a part of the optical fiber in the flexible body, and a hard distal member provided at a distal end of the flexible body and holding a distal end of the sheathing member.

14 Claims, 13 Drawing Sheets

(51) Int. Cl.
*G02B 23/26* (2006.01)
*A61B 90/00* (2016.01)
*A61B 34/20* (2016.01)
*A61B 90/30* (2016.01)

(52) U.S. Cl.
CPC ........ A61B 1/00045 (2013.01); A61B 1/0057 (2013.01); A61B 1/00078 (2013.01); G02B 23/26 (2013.01); *A61B 1/00009* (2013.01); *A61B 1/00071* (2013.01); *A61B 34/20* (2016.02); *A61B 2034/2061* (2016.02); *A61B 2090/067* (2016.02); *A61B 2090/306* (2016.02)

(56) References Cited

FOREIGN PATENT DOCUMENTS

| WO | WO 2014/188885 A1 | 11/2014 |
| WO | WO 2014/196524 A1 | 12/2014 |
| WO | WO 2015/163210 A1 | 10/2015 |

OTHER PUBLICATIONS

English translation of International Preliminary Report on Patentability dated Jul. 26, 2018 together with the Written Opinion received in related International Application No. PCT/JP2016/051027.

* cited by examiner

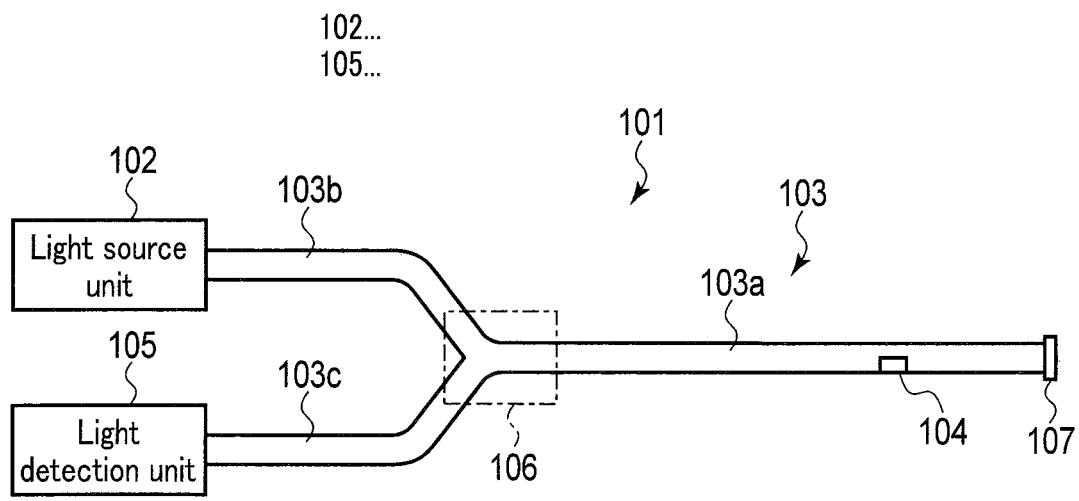
F I G. 1
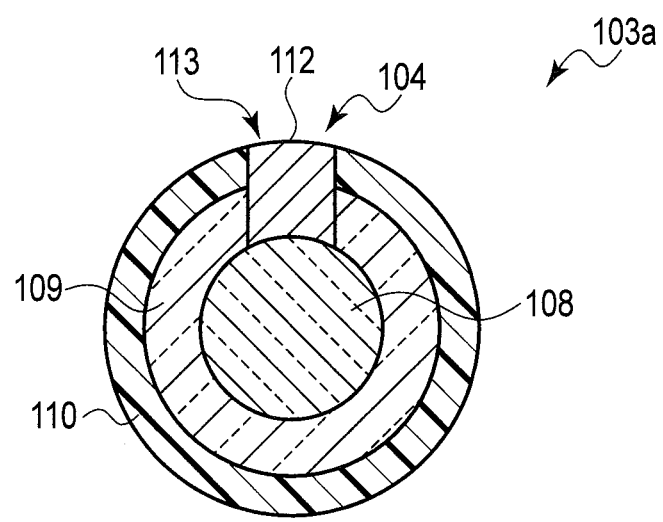
F I G. 2

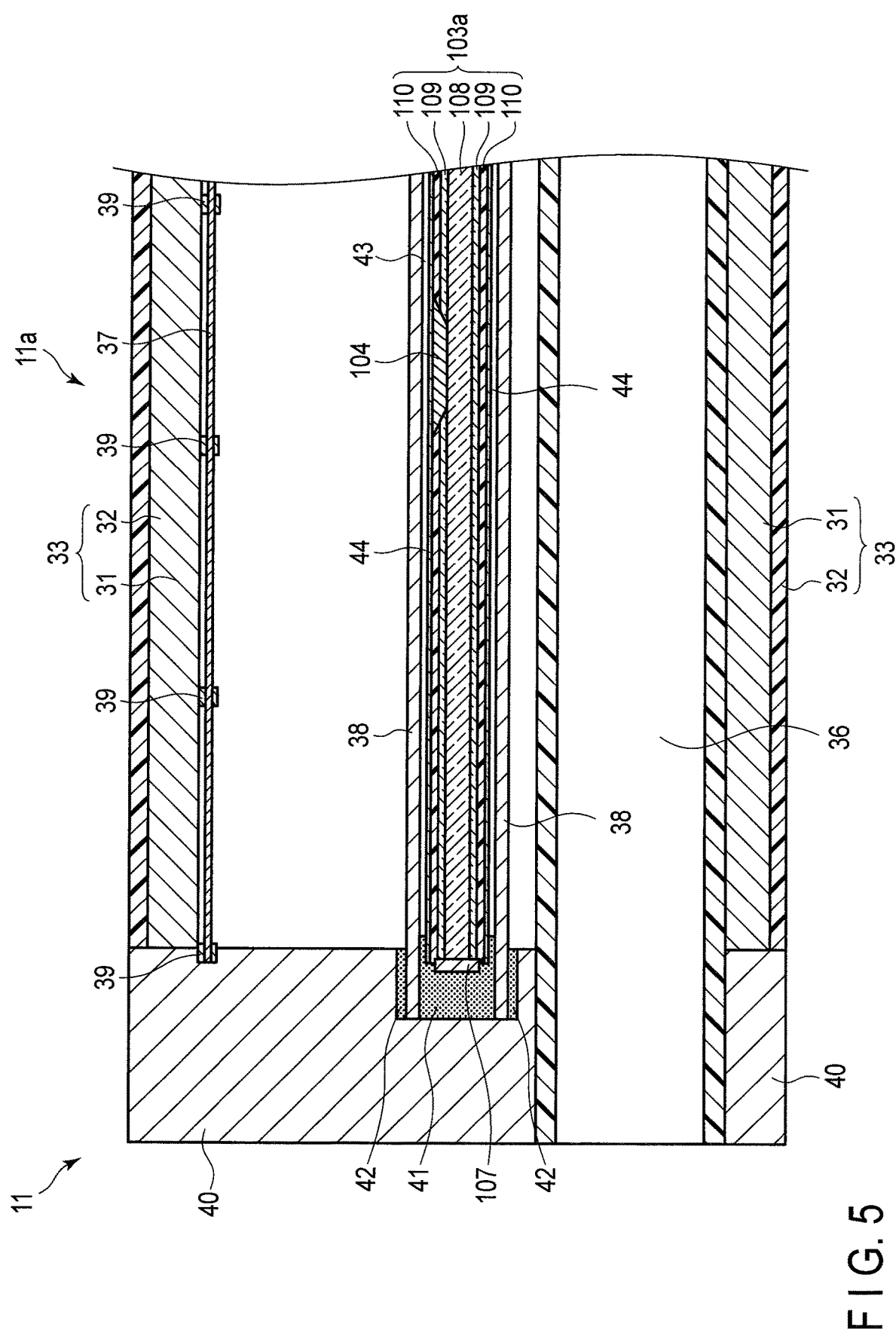
F I G. 5

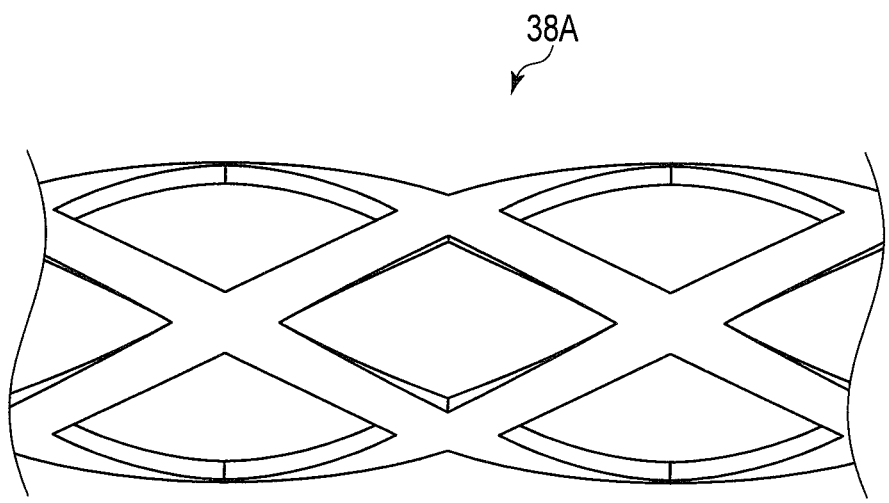
F I G. 12
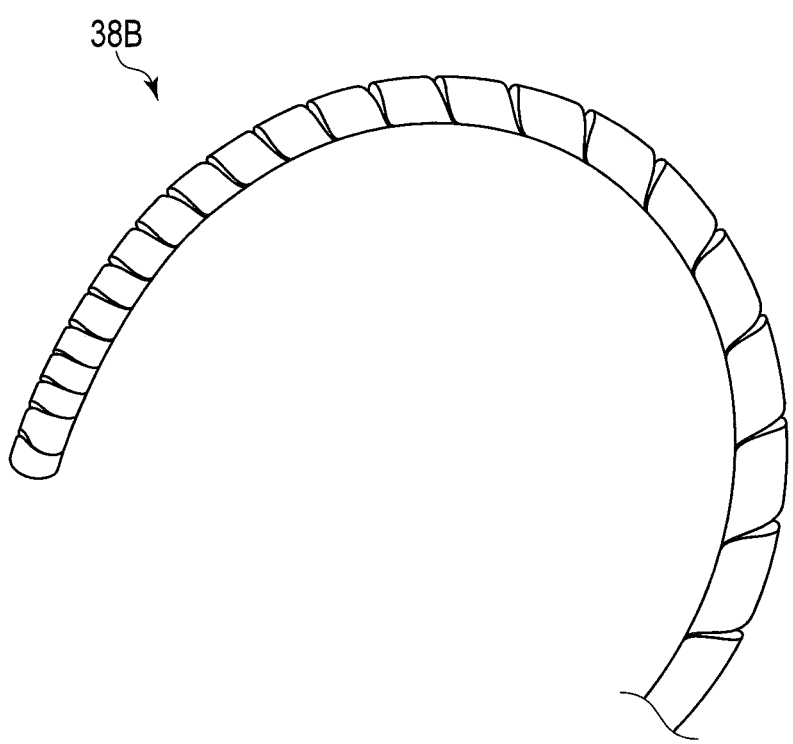
F I G. 13

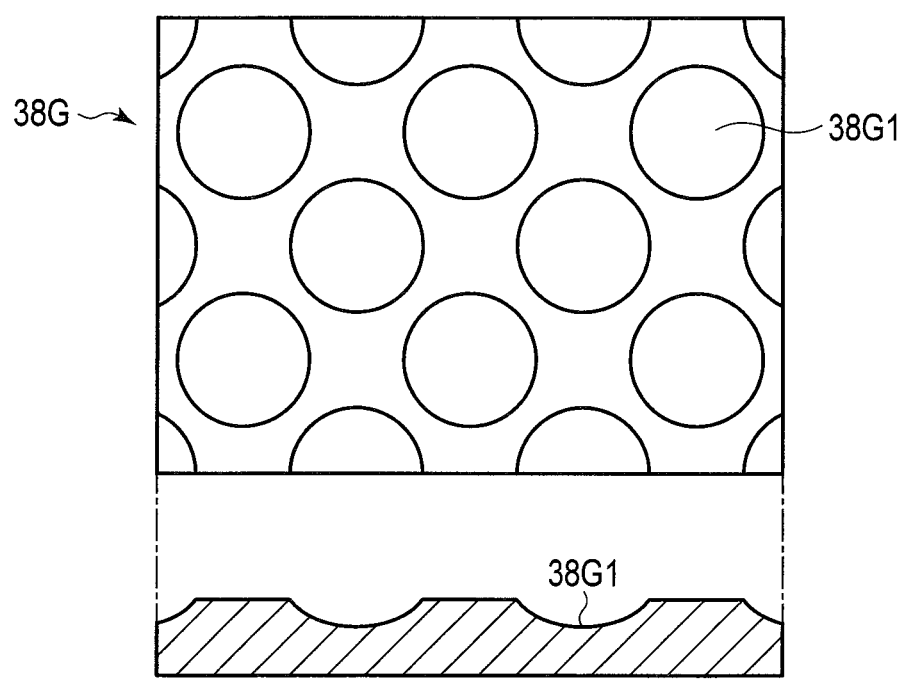
F I G. 18
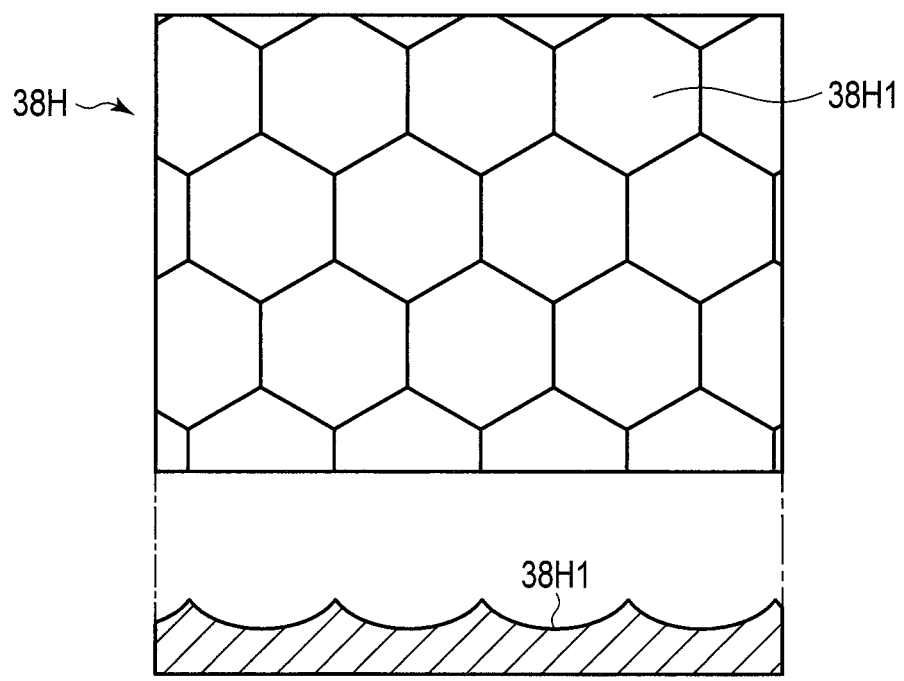
F I G. 19

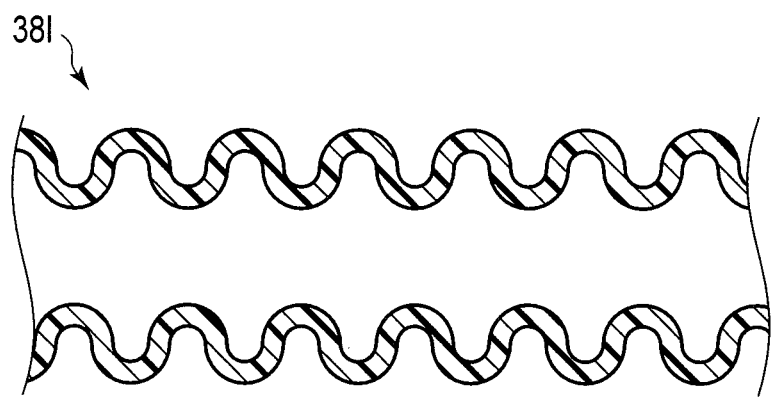
F I G. 20
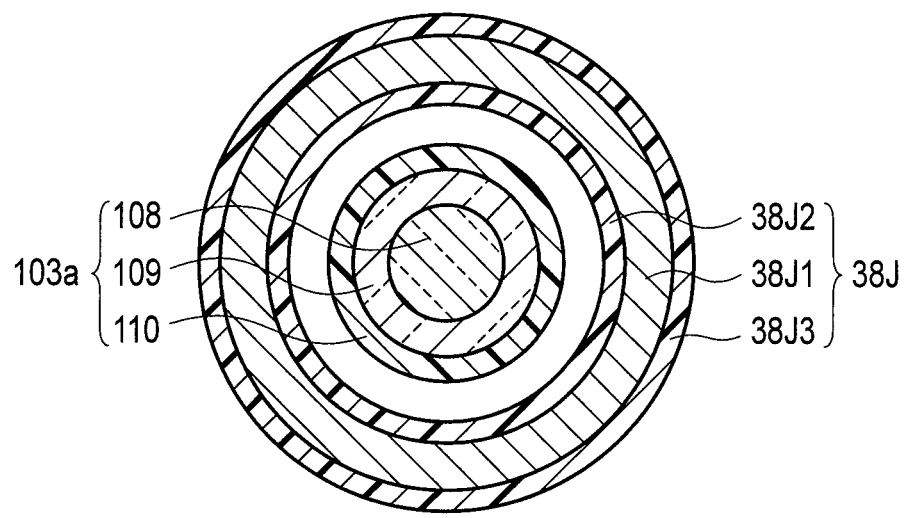
F I G. 21

SHAPE MEASURING CYLINDRICAL FLEXIBLE BODY APPARATUS

CROSS-REFERENCE TO RELATED APPLICATIONS

This application is a Continuation Application of PCT Application No. PCT/JP2016/051027, filed Jan. 14, 2016, the entire contents of which are incorporated herein by reference.

BACKGROUND OF THE INVENTION

1. Field of the Invention

The present invention relates to a shape measuring cylindrical flexible body apparatus including a cylindrical flexible body and a bend detection sensor to detect a bend of the cylindrical flexible body.

2. Description of the Related Art

In a cylindrical flexible body apparatus including a cylindrical flexible body, for example, in an endoscope apparatus including a flexible insertion section to be inserted in a subject, it is known that a bend of the insertion section is detected by incorporating a bend detection sensor. For example, Jpn. Pat. Appln. KOKAI Publication No. 2007-44402 discloses an endoscope apparatus in which curvature detection fibers including light loss portions to lose light in accordance with bend angles are provided in an insertion section. Each light loss portion is disposed at a predetermined position of the curvature detection fiber in a predetermined direction. The light transmission quantity of each curvature detection fiber varies depending on the curvature and direction of a bend of each light loss portion. Based on the light transmission quantity of each curvature detection fiber, a bend shape, i.e. a curvature and direction of a bend, of the insertion section in a portion where each light loss portion is located is calculated.

BRIEF SUMMARY OF THE INVENTION

A shape measuring cylindrical flexible body apparatus includes a cylindrical flexible body having a distal end and a proximal end, a bend detection sensor including a light source unit to radiate detection light, an optical fiber extending along a longitudinal direction of the cylindrical flexible body and configured to guide the detection light radiated from the light source unit, at least one detection target provided in the optical fiber and configured to vary characteristics of the detection light in accordance with a curvature of the optical fiber, and a light detection unit to detect the detection light guided through the optical fiber, a shape calculating device to calculate a bend shape of the cylindrical flexible body, based on the variation of the characteristics of the detection light detected by the light detection unit, a cylindrical sheathing member disposed in an inside of the cylindrical flexible body, the cylindrical sheathing member being a cylindrical member to sheathe at least a part of the optical fiber, and a hard distal member provided at the distal end of the cylindrical flexible body and holding a distal end of the cylindrical sheathing member.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 schematically shows a bend detection sensor.

FIG. 2 is a cross-sectional view in a radial direction of a curvature detection optical fiber.

FIG. 5 is a partial cross-sectional view in a longitudinal direction of the insertion section, taken along line B-O-B in FIG. 4.

FIG. 12 shows a cylindrical sheathing member in a second embodiment.

FIG. 13 shows another cylindrical sheathing member in the second embodiment.

FIG. 18 shows a cylindrical sheathing member in a fifth embodiment.

FIG. 19 shows another cylindrical sheathing member in the fifth embodiment.

FIG. 20 shows a cylindrical sheathing member in a sixth embodiment.

FIG. 21 shows a cylindrical sheathing member in a seventh embodiment.

DETAILED DESCRIPTION OF THE INVENTION

First Embodiment

Figure 3:
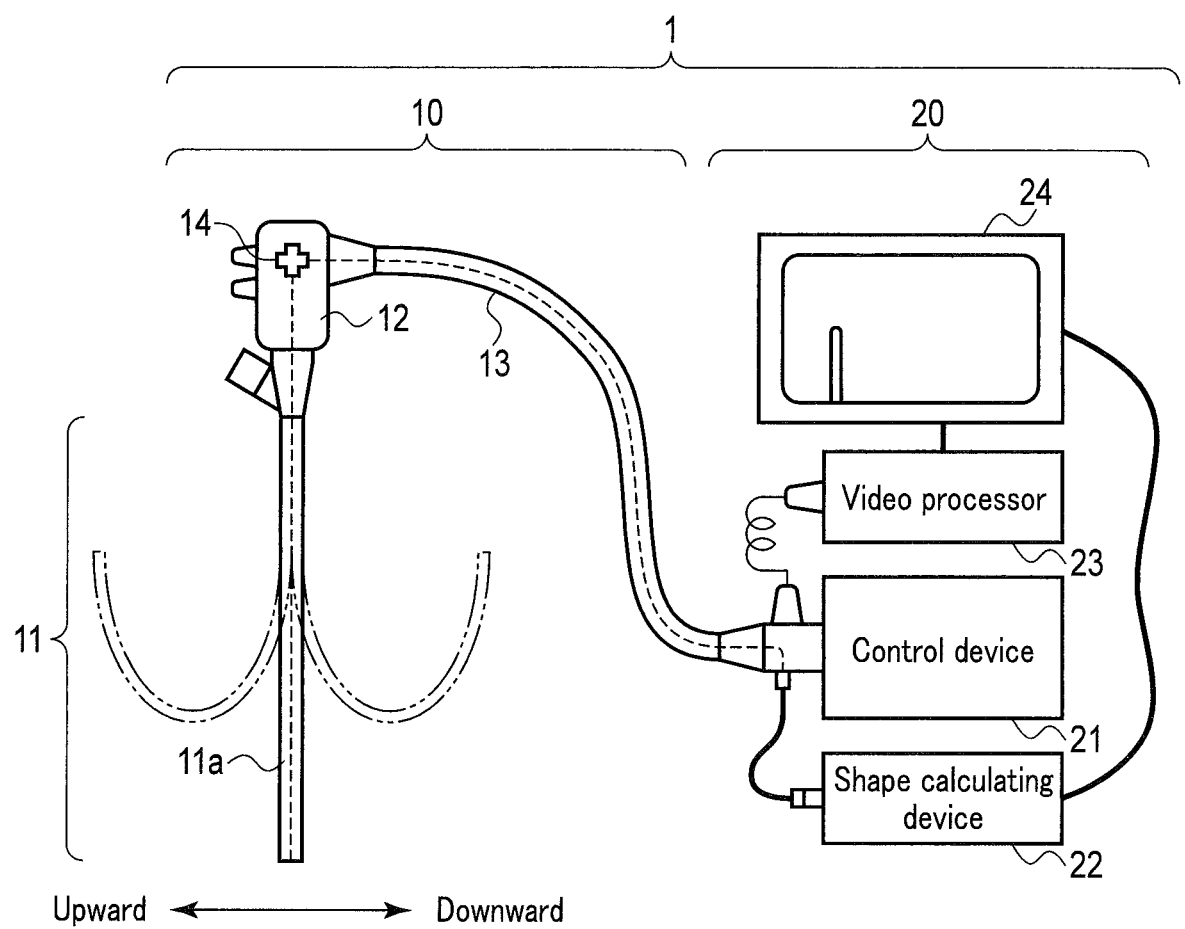
FIG. 3 schematically shows an endoscope apparatus in which the bend detection sensor is incorporated.

An endoscope apparatus 1, which is a shape measuring cylindrical flexible body apparatus according to a first embodiment of the present invention, is incorporated with a bend detection sensor 101. To begin with, the configuration and operation of the bend detection sensor 101 will be described.

FIG. 1 schematically shows the bend detection sensor 101. The bend detection sensor 101 includes a light source unit 102 to radiate detection light having desired wavelength characteristics, an optical fiber 103 for bend detection to guide detection light radiated from the light source unit 102, and a light detection unit 105 to detect detection light guided through the optical fiber 103. The optical fiber 103 is connected to the light source unit 102 and light detection unit 105. The light source unit 102 includes, for example, an LED light source or a laser light source. The light detection unit 105 includes a light detector to photoelectrically convert detection light.

The optical fiber 103 has flexibility and is composed of a curvature detection optical fiber 103a, a light supply optical fiber 103b and a light reception optical fiber 103c, which are branched in three directions by a coupler (optical coupler) 106. Specifically, the optical fiber 103 is formed by connecting the light supply optical fiber 103b and light reception optical fiber 103c to the curvature detection optical fiber 103a by the coupler 106. A proximal end of the light supply optical fiber 103b is connected to the light source unit 102. In addition, a reflector 107, which reflects guided light, is provided on a distal end of the curvature detection optical fiber 103a. The reflector 107 is, for example, a mirror. A proximal end of the light reception optical fiber 103c is connected to the light detection unit 105.

The light supply optical fiber 103b guides detection light, which is radiated from the light source unit 102, to the coupler 106. The coupler 106 brings most of the incoming detection light from the light supply optical fiber 103b to the curvature detection optical fiber 103a. The curvature detection optical fiber 103a guides the detection light from the coupler 106 to the reflector 107, and guides the detection light that is reflected by the reflector 107 to the coupler 106. The coupler 106 brings at least part of the detection light from the curvature detection optical fiber 103a to the light reception optical fiber 103c. The light reception optical fiber 103c guides the light from the coupler 106 to the light detection unit 105. The light detection unit 105 photoelectrically converts the detection light received from the light reception optical fiber 103c to output an electric signal indicative of a reception light quantity.

FIG. 2 is a cross-sectional view in a radial direction of the curvature detection optical fiber 103a. The curvature detection optical fiber 103a includes a core 108, a cladding 109 covering an outer peripheral surface of the core 108, and a cover 110 covering an outer peripheral surface of the cladding 109. In addition, the curvature detection optical fiber 103a is provided with at least one detection target 104. The detection target 104 is provided on only a part of the outer periphery of the curvature detection optical fiber 103a, and configured to vary the characteristics of the detection light passing through the detection target 104 in accordance with the bend shape, i.e. the curvature and direction of a bend, of the curvature detection optical fiber 103a.

The detection target 104 includes an optical aperture 112 in which the core 108 is exposed by removing parts of the cover 110 and cladding 109, and an optical characteristic conversion member 113 formed in the optical aperture 112. Note that the optical aperture 112 is not necessarily required to expose the core 108, and the optical aperture 112 may not expose the core 108 if the light passing through the curvature detection optical fiber 103a reaches the optical aperture 112. The optical characteristic conversion member 113 is a member to convert optical characteristics (light quantity, wavelength, etc.) of the light guided through the curvature detection optical fiber 103a, and is, for example, a guided-light loss member (light absorber) or a wavelength conversion member (fluorescent substance). In the description below, it is assumed that the optical characteristic conversion member is a guided-light loss member.

If the detection light propagating through the curvature detection optical fiber 103a enters the optical characteristic conversion member 113 of the detection target 104, part of the detection light is absorbed by the optical characteristic conversion member 113. Thus, there occurs a loss of the detection light guided by the curvature detection optical fiber 103a. The loss quantity of the guided light varies in accordance with the amount of bend of the curvature detection optical fiber 103a.

For example, even when the curvature detection optical fiber 103a is in a straight state, a certain quantity of detection light is lost by the optical characteristic conversion member 113 in accordance with the width, length, etc. of the optical aperture 112. The quantity of loss of light in the straight state is set as a reference. If the optical characteristic conversion member 113 is disposed on an outside with a relatively large radius of curvature in a bent state of the curvature detection optical fiber 103a, there occurs a greater quantity of loss of guided light than the quality of loss of guided light that is set as the reference. On the other hand, if the optical characteristic conversion member 113 is disposed on an inside with a relatively small radius of curvature in a bent state of the curvature detection optical fiber 103a, there occurs a less quantity of loss of guided light than the quality of loss of guided light that is set as the reference.

The variation of the quality of loss of guided light is reflected on the quantity of detection light received by the light detection unit 105, i.e. on an output signal of the light detection unit 105. Accordingly, it is possible to calculate, based on the output signal of the light detection unit 105, the bend shape of the curvature detection optical fiber 103a at the position of the detection target 104, i.e. at the position where the optical characteristic conversion member 113 is provided.

In FIG. 1 and FIG. 2, only one detection target 104 is illustrated. However, the curvature detection optical fiber 103a may be provided with detection targets 104 that are disposed at intervals along the axis of the curvature detection optical fiber 103a. Thereby, the bend can be detected at positions along the axis of the curvature detection optical fiber 103a. Alternatively, two detection targets 104 may be provided at positions that are substantially identical along the axis of the curvature detection optical fiber 103a and are different along the circumference of the curvature detection optical fiber 103a (e.g. at mutually perpendicular positions). Thereby, not only a bend in one direction but also bends in mutually perpendicular two directions can be calculated. When the curvature detection optical fiber 103a is provided with detection targets 104, for example, the detection targets 104 are configured to vary characteristics of light of mutually different wavelengths, the light source unit 102 is configured to radiate detection light including wavelength components corresponding to the detection targets 104, or radiates detection light that is wavelength-swept, and the light detection unit 105 is configured to detect the detection light with respect to each of the wavelength components corresponding to the detection targets 104.

Next, the configuration of the endoscope apparatus 1 will be described. FIG. 3 schematically shows the endoscope apparatus 1. The endoscope 1 includes a scope 10, in which at least the curvature detection optical fiber 103a of the bend detection sensor 101 is incorporated, and a main body 20. The main body 20 includes a control device 21, a shape calculating device 22, a video processor 23, and a display 24. The control device 21 controls predetermined functions of the scope 10, shape calculating device 22, and video processor 23, and predetermined functions of peripheral devices connected to these components.

The scope 10 includes a flexible insertion section 11 to be inserted in a subject, and a control section 12 provided on a proximal end side of the insertion section 11. The insertion section 11 has a bendable section 11a at a distal end portion thereof, the bendable section 11a being bendable in at least two specific directions (e.g. upward and downward directions). A cord 13 extends from the control section 12. The scope 10 is detachably connected to the main body 20 through the cord 13, and communicates with the main body 20. The control section 12 is provided with an operation dial 14 to input an operation for bending the bendable section 11a of the insertion section 11 in at least two specific directions (e.g. upward and downward directions) at a desired curvature. The cord 13 contains a camera cable 34, a light guide fiber 35, etc., which will be described later.

Although the bend detection sensor 101 is shown in FIG. 3, the endoscope apparatus 1 includes the bend detection sensor 101 shown in FIG. 1. Specifically, the endoscope apparatus 1 is a shape measuring cylindrical flexible body apparatus including the bend detection sensor 101 to detect a bend of the bendable section 11a of the insertion section 11, which is a cylindrical flexible body.

The curvature detection optical fiber 103a of the bend detection sensor 101 is attached along an elongated cylindrical flexible body, which is an object to be detected, in this embodiment, the insertion section 11 of the scope 10 (to be described later). At a time of attachment, the detection target 104 of the curvature detection optical fiber 103a is aligned with a desired detection position of the insertion section 11, and the curvature detection optical fiber 103a is attached in a proper position of the insertion section 11. The curvature detection optical fiber 103a bends in a manner to follow a bending movement of the bendable section 11a of the insertion section 11. The characteristics, for example, light quantity, of the detection light, which passes through the detection target 104 and is detected by the light detection unit 105, vary in accordance with a variation of the curvature of the curvature detection optical fiber 103a at a peripheral portion of the detection target 104. The light detection unit 105 outputs a signal of the received light quantity. The output signal of the light detection unit 105 includes information of the bend of the bendable section 11a of the insertion section 11.

The shape calculating device 22 is connected to the light detection unit 105. The shape calculating device 22 receives an output signal from the light detection unit 105, and calculates, based on the output signal, the bend shape of the bendable section 11a of the insertion section 11. In other words, the shape calculating device 22 calculates the bend shape of the bendable section 11a of the insertion section 11, based on the variation of the characteristics of the detection light detected by the light detection unit 105. The calculated bend shape is transmitted from the shape calculating device 22 to the display 24, and is displayed on the display 24.

The video processor 23 image-processes an electric signal that is acquired from an imaging element (not shown) at a distal end of the scope through the camera cable 34 and the control device 21, which are described later. The display 24 displays an image of the inside of the subject, which has been processed by the video processor 23.

Figure 4:
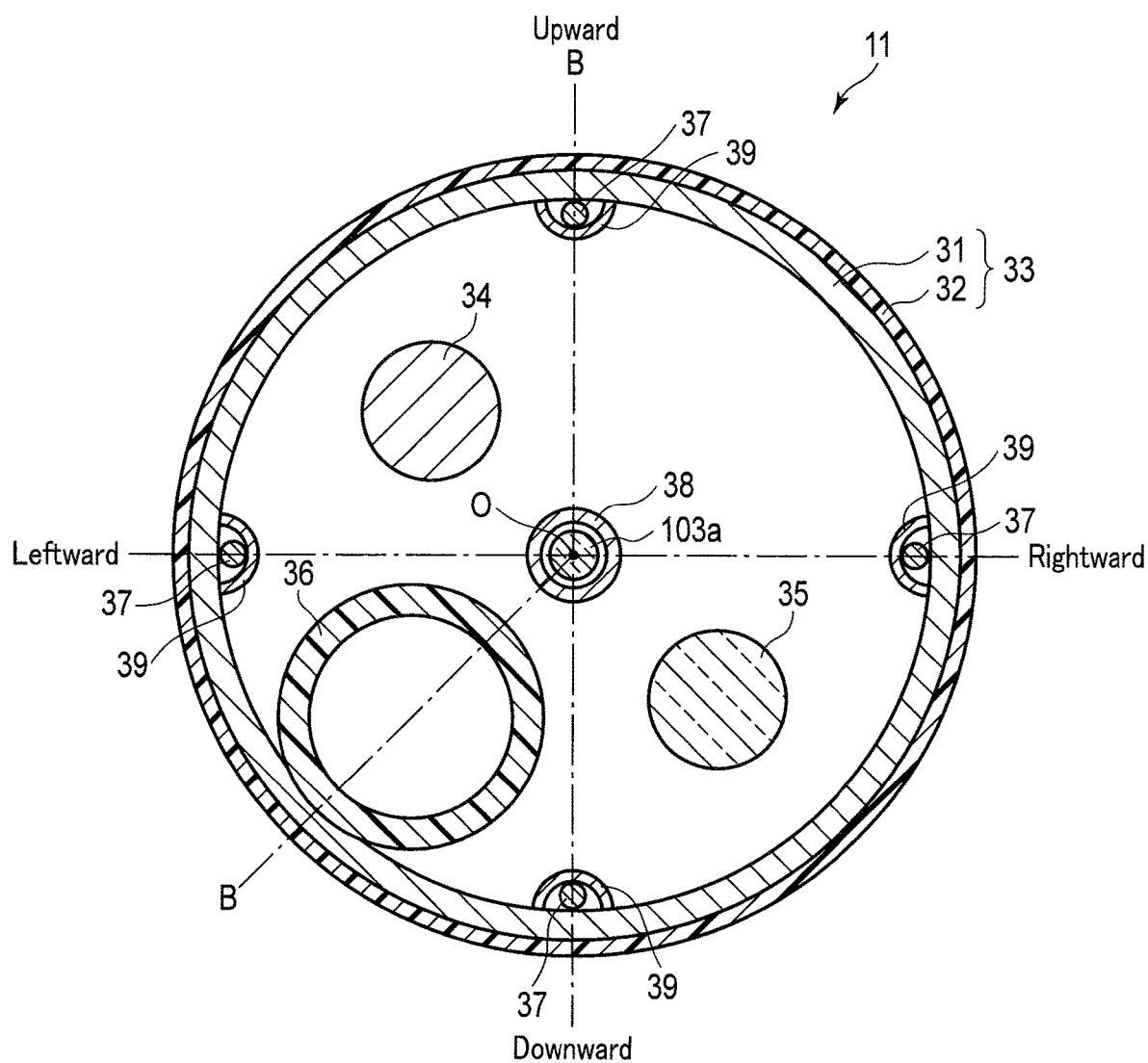
FIG. 4 is a cross-sectional view in a radial direction of an insertion section in a first embodiment.
Figure 6:
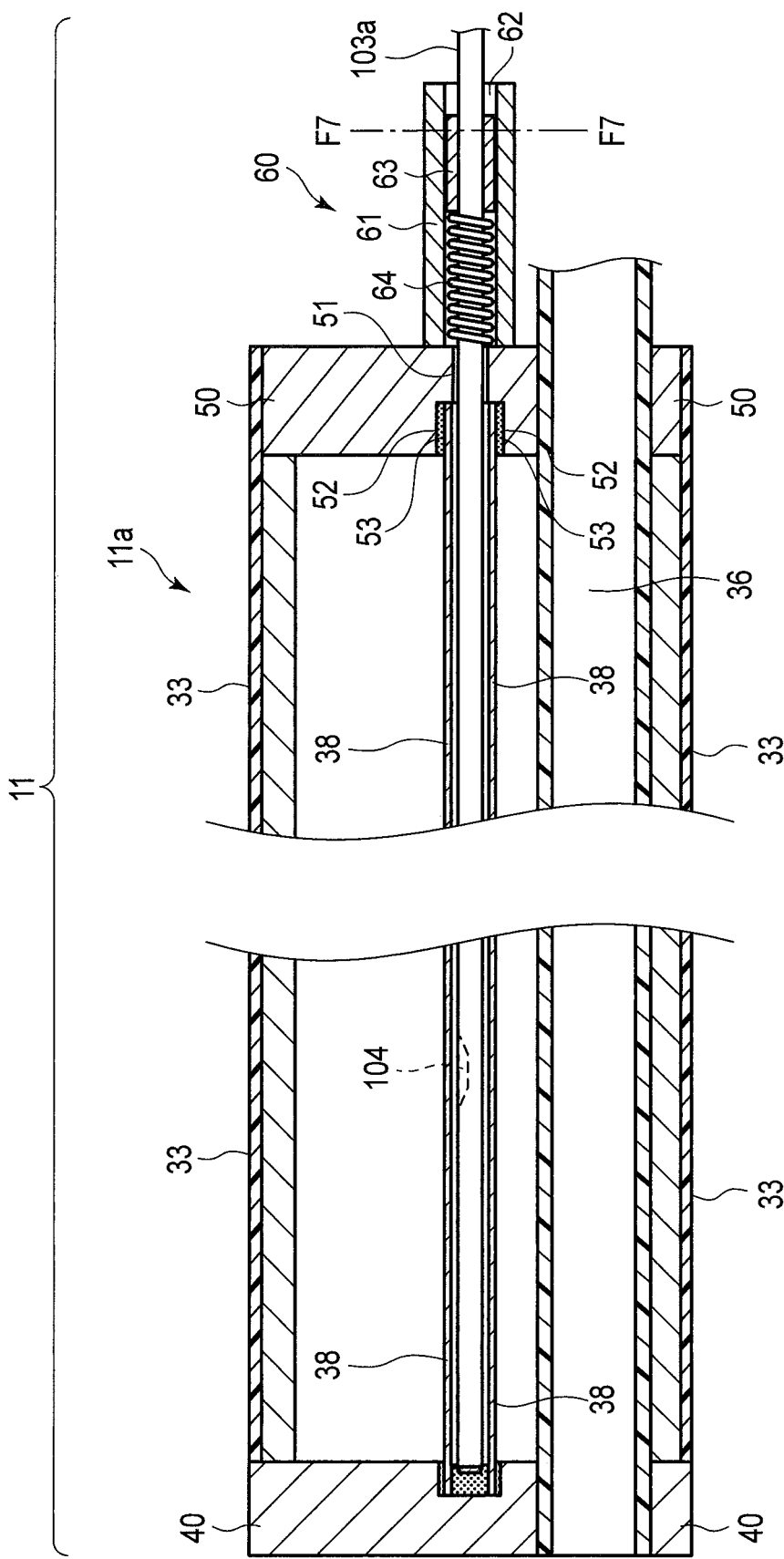
FIG. 6 is a cross-sectional view corresponding to FIG. 5, FIG. 6 schematically showing the entire configuration of a bendable section of the insertion section in the first embodiment.
Figure 7:
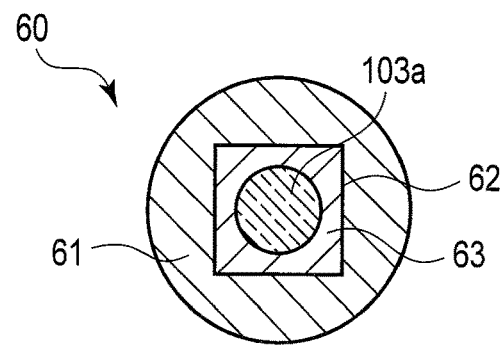
FIG. 7 is a cross-sectional view taken along line F7-F7 in FIG. 6.

FIG. 4 is a cross-sectional view in a radial direction of the insertion section 11 in the first embodiment. FIG. 5 is a cross-sectional view in a longitudinal direction of the bendable section 11a of the insertion section 11, taken along line B-O-B in FIG. 4. FIG. 6 is a cross-sectional view corresponding to FIG. 5, FIG. 6 schematically showing the entire configuration of the bendable section of the insertion section in the first embodiment. FIG. 7 is a cross-sectional view taken along line F7-F7 in FIG. 6.

The insertion section 11 is configured such that a camera cable 34, a light guide fiber 35, a channel tube 36, an operation wire 37, and the curvature detection optical fiber 103a, which is inserted in a cylindrical sheathing member 38, are built in an elongated hollow member 33. The elongated hollow member 33 is composed of a bendable elongated coil 31, and a covering tube 32 with flexibility that is covered on an outer peripheral surface of the elongated coil 31.

The camera cable 34 is an electrical wire that is connected to the imaging element (not shown) at the distal end of the scope and the control device 21, and configured to transmit an electric signal. The light guide fiber 35 is a light guide member that is connected to an illuminator (not shown) at the distal end of the scope and to a light source (not shown) in the control device 21, and configured to guide illumination light from the light source to the illuminator. The channel tube 36 is a cylindrical tube for passing a treatment instrument such as an ultrasonic probe or a forceps.

The operation wire 37 is provided along the axis in the insertion section 11 in order to perform an operation of bending the bendable section 11a of the insertion section 11 in a desired direction at a desired curvature. A wire receiver 39 having, for example, a substantially semicircular space is attached to an inner peripheral surface of the elongated coil 31, and the operation wire 37 is passed through the space between the wire receiver 39 and the elongated coil 31. A distal end of the operation wire 37 is fixed to a distal end of the insertion section 11, and a proximal end of the operation wire 37 is coupled to the operation dial 14 of the control section 12. Thereby, an operation of the operation dial 14 is transmitted to the bendable section 11a. If an operator operates the operation dial 14 and the operation wire 37 is moved, the bendable section 11a of the insertion section 11 is bent.

In the present embodiment, as shown in FIG. 4, since four operation wires 37 are disposed one by one in four directions, namely in upward, downward, leftward, and rightward directions, four wire receivers 39 corresponding to the four operation wires 37 are provided. For example, if the upward operation wire 37 is pulled by a rotational operation of the operation dial 14, the bendable section 11a of the insertion section 11 bends upward. If the downward operation wire 37 is pulled by a rotational operation of the operation dial 14, the bendable section 11a of the insertion section 11 bends downward. In this manner, by pulling the operation wire 37 for each direction by a desired amount by the rotation of the operation dial 14, the bend direction and curvature of the bendable section 11a of the insertion section 11 are controlled.

Besides, as shown in FIG. 5, an insertion section distal member 40, which is hard and includes the imaging element, illuminator, etc. (not shown), is disposed at the distal end of the insertion section 11. At least distal ends of the channel tube 36, operation wire 37, cylindrical sheathing member 38, and curvature detection optical fiber 103a are held by the insertion section distal member 40. Although not shown in FIG. 5, at least distal ends of the camera cable 34 and light guide fiber 35 are also held by the insertion section distal member 40.

The cylindrical sheathing member 38 is disposed at about the center in the radial direction of the elongated hollow member 33. For example, the center axis of the cylindrical sheathing member 38 substantially coincides with the center axis of the elongated hollow member 33. The cylindrical sheathing member 38 sheathes or covers the curvature detection optical fiber 103a. The curvature detection optical fiber 103a, too, is disposed at about the center in the radial direction of the insertion section 11 (elongated hollow member 33). The center axis of the curvature detection optical fiber 103a also substantially coincides with the center axis of the insertion section 11 (elongated hollow member 33). The cylindrical sheathing member 38 has a flexibility that is equal to or greater than the flexibility of the curvature detection optical fiber 103a. The cylindrical sheathing member 38 has a torsional rigidity that is higher than the torsional rigidity of the curvature detection optical fiber 103a.

A distal end portion of the curvature detection optical fiber 103a is fixed to a distal end portion of the cylindrical sheathing member 38 by an adhesive 41. In addition, the distal end portion of the cylindrical sheathing member 38 is fixed to the insertion section distal member 40 by an adhesive 42. The adhesive 41 adheres the curvature detection optical fiber 103a and cylindrical sheathing member 38, and adheres the curvature detection optical fiber 103a and insertion section distal member 40. The adhesive 41, 42 may be an epoxy adhesive or the like, of which high adhesive strength can be expected. Since only the distal end portion of the curvature detection optical fiber 103a is fixed to the cylindrical sheathing member 38, the curvature detection optical fiber 103a is movable in the axial direction in the cylindrical sheathing member 38.

The cylindrical sheathing member 38 may be a resin tube such as a fluororesin tube with flexibility of PTFE, etc., a polyamide tube or a PEEK tube, or a metallic tube of NiTi, SUS, brass, etc.

A proper space 43 is formed between the cylindrical sheathing member 38 and curvature detection optical fiber 103a in order to reduce a contact therebetween. Specifically, an inside diameter of the cylindrical sheathing member 38 is set to be greater than an outside diameter of the cover 110 of the curvature detection optical fiber 103a. In order to reduce the frictional resistance between the cylindrical sheathing member 38 and curvature detection optical fiber 103a, a solid lubricant 44 lies between the cylindrical sheathing member 38 and curvature detection optical fiber 103a. For example, the solid lubricant 44 is coated on the surface of the curvature detection optical fiber 103a. The solid lubricant 44 may be, for example, molybdenum sulfide, boron carbide, boron nitride, fluorine powder, or carbon powder. If necessary, the solid lubricant 44 may be filled in the space 43.

In addition, as shown in FIG. 6, a bendable section rear-end portion 50 is disposed at a rear end of the bendable section 11a. The elongated hollow member 33 is attached to the bendable section rear-end portion 50. The bendable section rear-end portion 50 includes a through hole 51 for passing the curvature detection optical fiber 103a, and a recess portion 52 to receive the cylindrical sheathing member 38. A rear end portion of the cylindrical sheathing member 38 is fixed to the bendable section rear-end portion 50 by an adhesive 53. The cylindrical sheathing member 38 sheathes or covers the curvature detection optical fiber 103a over at least the entire length of the bendable section 11a.

Preferably, a tension applying mechanism 60, which is configured to apply tension to the curvature detection optical fiber 103a in a longitudinal direction thereof, is provided on the bendable section rear-end member 50. The tension applying mechanism 60 includes a guide member 61 having a guide hole 62, and a movable member 63 and an elastic member 64, which are contained in the guide hole 62 of the guide member 61. The curvature detection optical fiber 103a extends through the guide hole 62 of the guide member 61. The movable member 63 is fixed to the curvature detection optical fiber 103a. The elastic member 64 may be, for example, a coil spring, and has a greater diameter than the through hole 51. The elastic member 64 is disposed in a compressed state between the bendable section rear-end member 50 and movable member 63 in the guide hole 62 of the guide member 61. Thereby, the movable member 63 is pushed by the restoring force of the elastic member 64 toward the rear end of the insertion section 11, i.e. toward the control section 12. As a result, the curvature detection optical fiber 103a extends in the cylindrical sheathing member 38 without slacking.

As shown in FIG. 7, the guide hole 62 of the guide member 61 has a rectangular cross section perpendicular to the axis thereof. The movable member 63 has such a rectangular prismatic outer shape as to just fit in the guide hole 62. Thus, the movable member 63 can axially move in the guide hole 62 of the guide member 61, but cannot rotate about the axis. Thereby, the curvature detection optical fiber 103a is prevented from twisting. Specifically, the movable member 63 and guide hole 62 cooperate to constitute a twist prevent mechanism to prevent the curvature detection optical fiber 103a from twisting about the longitudinal axis thereof.

If the bendable section 11a of the insertion section 11 of the scope 10 bends by the rotation operation of the operation dial 14 or by being pushed in the subject, since the curvature detection optical fiber 103a and cylindrical sheathing member 38 are located on the center axis of the bendable section 11a, the curvature detection optical fiber 103a and cylindrical sheathing member 38 bend in shapes similar to the shape of the bendable section 11a. In addition, since other built-in components, such as the camera cable 34, light guide fiber 35, and channel tube 36, deviate from the center axis of the bendable section 11a, these components bend and move. However, since the curvature detection optical fiber 103a is sheathed by the cylindrical sheathing member 38, the other built-in components, such as the camera cable 34, light guide fiber 35, and channel tube 36, do not come in direct contact with the curvature detection optical fiber 103a. Accordingly, the curvature detection optical fiber 103a does not directly receive a torque from the other built-in components. In short, the cylindrical sheathing member 38 has a function of preventing the curvature detection optical fiber 103a from twisting.

It is possible that the other built-in components, such as the camera cable 34, light guide fiber 35, and channel tube 36, come in contact with the cylindrical sheathing member 38, and the cylindrical sheathing member 38 receives a torque. However, the cylindrical sheathing member 38 has a torsional rigidity that is higher than the torsional rigidity of the curvature detection optical fiber 103*a*, and does not easily twist. Moreover, even when a twist occurs in the cylindrical sheathing member 38, the solid lubricant 44 lies between the cylindrical sheathing member 38 and the curvature detection optical fiber 103*a*, and the frictional resistance is reduced. Therefore, the curvature detection optical fiber 103*a* does not easily receive a torque.

Therefore, in the endoscope apparatus 1 of the present embodiment, a twist does not easily occur in the curvature detection optical fiber 103*a* of the bend detection sensor 101. Thereby, a decrease in detection precision of a bend of the bendable section 11*a* of the insertion section 11, which occurs due to the occurrence of a twist of the curvature detection optical fiber 103*a*, is effectively avoided. Accordingly, this endoscope apparatus 1 can exactly calculate the bend shape of the bendable section 11*a* of the insertion section 11. Specifically, a shape measuring cylindrical flexible body apparatus that can calculate the bend shape of the cylindrical flexible body with a higher precision than in the conventional art is provided.

[Modifications of Curvature Detection Optical Fiber 103*a*]

Figure 8:
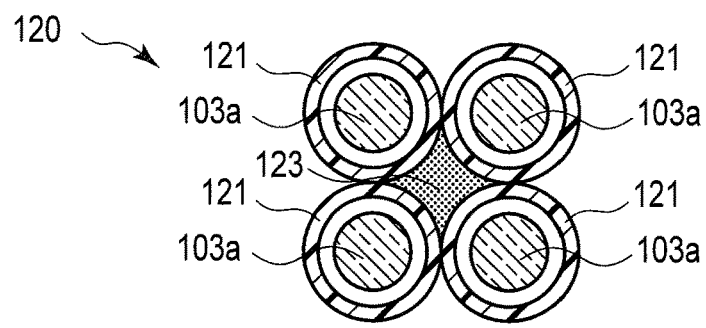
FIG. 8 shows a curvature detection optical fiber group, which is applicable in place of the curvature detection optical fiber.

In the above-described embodiment, the curvature detection optical fiber 103*a* is built in the inside of the insertion section 11. Alternatively, curvature detection optical fibers 103*a* may be built in the inside of the insertion section 11. FIG. 8 shows a curvature detection optical fiber group 120 that is applicable in place of the curvature detection optical fiber 103*a* shown in, for example, FIG. 5. The curvature detection optical fiber group 120 includes curvature detection optical fibers 103*a*, e.g. four curvature detection optical fibers 103*a*. Each curvature detection optical fiber 103*a* is sheathed by a cylindrical sheathing member 121. A space is provided between each curvature detection optical fiber 103*a* and each cylindrical sheathing member 121. A solid lubricant may be filled in this space. The four cylindrical sheathing members 121 extend along the axis in contact with each other, and are adhered by, for example, an adhesive 123. Alternatively, the four cylindrical sheathing members 121 may be bundled by a bundling tool such as a band. The curvature detection optical fiber group 120 may be applied, for example, in place of the curvature detection optical fiber 103*a*. Specifically, the curvature detection optical fiber group 120 may be inserted in the cylindrical sheathing member 38. In another example, the curvature detection optical fiber group 120 may be applied in place of the curvature detection optical fiber 103*a* and the cylindrical sheathing member 38. In this case, the cylindrical sheathing members 121 function in place of the cylindrical sheathing member 38.

Figure 9:
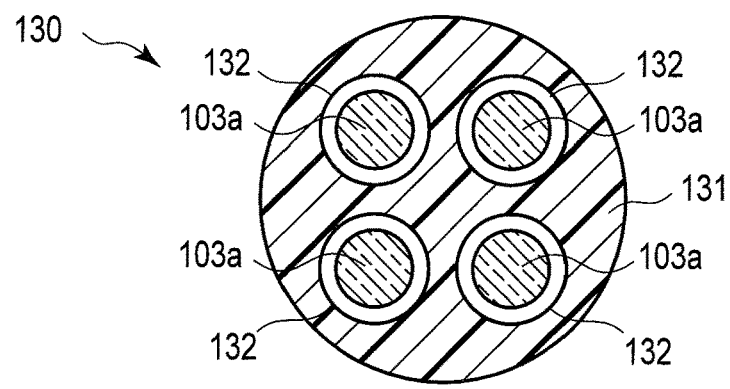
FIG. 9 shows another curvature detection optical fiber group, which is applicable in place of the curvature detection optical fiber.

FIG. 9 shows another curvature detection optical fiber group 130 that is applicable in place of the curvature detection optical fiber 103*a* shown in, for example, FIG. 5. The curvature detection optical fiber group 130 includes curvature detection optical fibers 103*a*, e.g. four curvature detection optical fibers 103*a*. The curvature detection optical fibers 103*a* are sheathed by a cylindrical sheathing member 131. The cylindrical sheathing member 131 is a multi-lumen tube including four small lumens (lumen cavities) 132. Each small lumen has a circular cross section perpendicular to the axis thereof. Each curvature detection optical fiber 103*a* is inserted in a small lumen 132. A space is provided between each curvature detection optical fiber 103*a* and each small lumen 132. A solid lubricant may be filled in this space. The curvature detection optical fiber group 130 may be applied, for example, in place of the curvature detection optical fiber 103*a*. Specifically, the curvature detection optical fiber group 130 may be inserted in the cylindrical sheathing member 38. In another example, the curvature detection optical fiber group 130 may be applied in place of the curvature detection optical fiber 103*a* and the cylindrical sheathing member 38. In this case, the cylindrical sheathing member 131 functions in place of the cylindrical sheathing member 38.

When the curvature detection optical fiber group 120, 130 is used, each curvature detection optical fiber 103*a* is connected to the light source unit 102 and light detection unit 105 through the light supply optical fiber 103*b* and light reception optical fiber 103*c*, respectively. In association with the four curvature detection optical fibers 103*a*, for example, the light source unit 102 may include four light sources, and the light detection unit 105 may include four light detectors. The use of the curvature detection optical fiber group 120, 130 facilitates an increase in detection targets 104.

[Modification of Fixation of Curvature Detection Optical Fiber 103*a*]

In the above-described embodiment, the curvature detection optical fiber 103*a* is fixed near the distal end of the bendable section 11*a*. In a modification, the curvature detection optical fiber 103*a* may be fixed near the rear end of the bendable section 11*a*. In this case, the tension applying mechanism 60 is provided in the insertion section distal member 40. In another modification, the curvature detection optical fiber 103*a* may be fixed in an intermediate portion between the distal end and rear end of the bendable section 11*a*. In short, it should suffice if the curvature detection optical fiber 103*a* is fixed at one location in the range of the entire length of the bendable section 11*a*.

Figure 10:
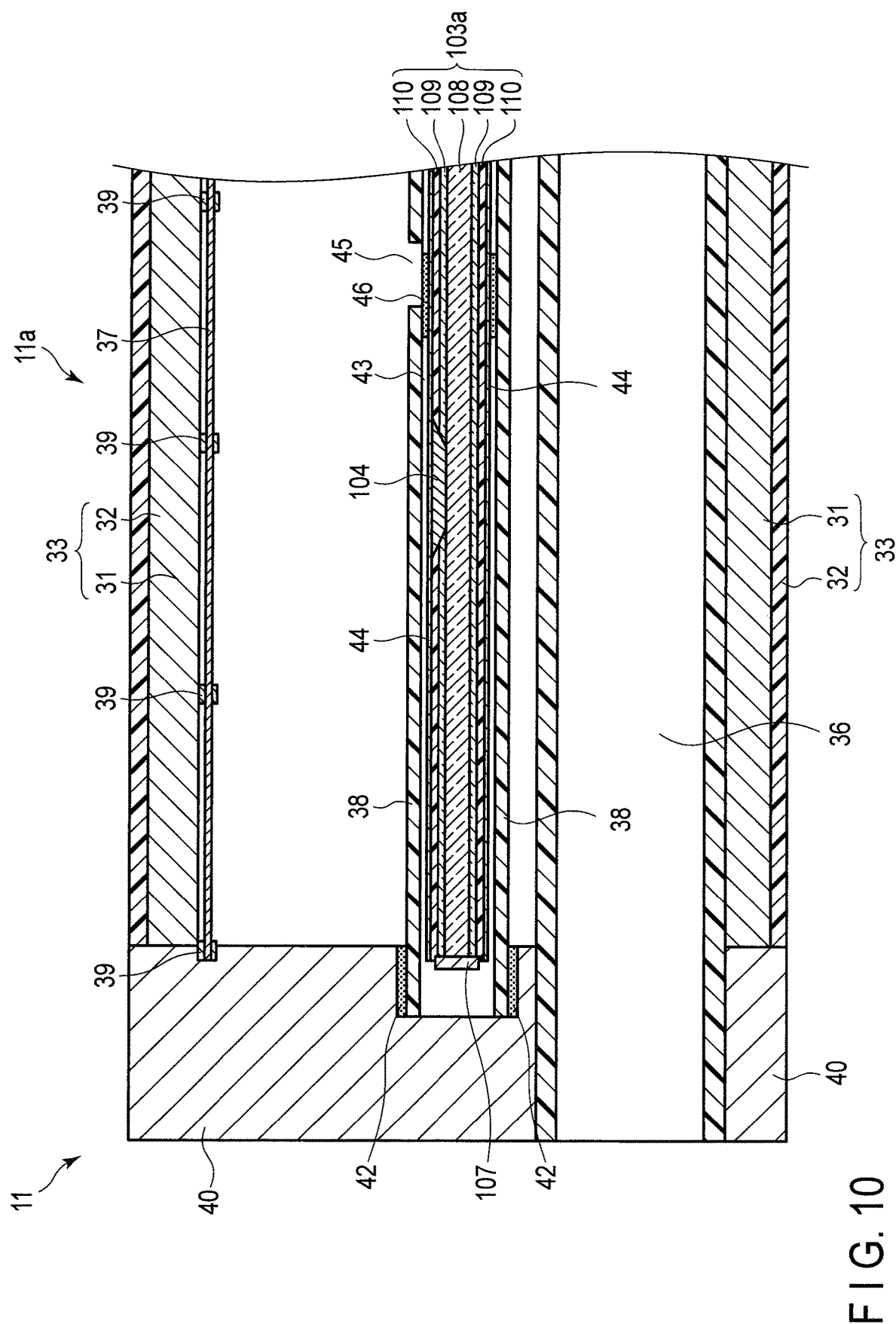
FIG. 10 is a partial cross-sectional view corresponding to FIG. 5, FIG. 10 schematically showing an insertion section relating to a modification in which the curvature detection optical fiber is fixed in an intermediate portion of the bendable section.

FIG. 10 is a partial cross-sectional view corresponding to FIG. 5, FIG. 10 showing the insertion section 11 relating to a modification in which the curvature detection optical fiber 103*a* is fixed in an intermediate portion of the bendable section 11*a*. As illustrated in FIG. 10, in the insertion section 11 according to this modification, the adhesive 41, which adheres the distal end portion of the curvature detection optical fiber 103*a* to the distal end portion of the cylindrical sheathing member 38, does not exist. The cylindrical sheathing member 38 is provided with a notch opening portion 45 in which a part of the cylindrical sheathing member 38 is cut out. The notch opening portion 45 is formed near a position where the curvature detection optical fiber 103*a* is fixed. The curvature detection optical fiber 103*a* is fixed to the cylindrical sheathing member 38 by an adhesive 46, which has been supplied from the notch opening portion 45.

The insertion section 11 according to this modification also includes, preferably, the tension applying mechanism 60. However, the tension applying mechanism 60 may be omitted, depending on cases. For example, when the curvature detection optical fiber 103*a* does not include the detection target 104 on the control section 12 side of the adhesive 46, the tension applying mechanism 60 is preferably omitted.

If the cylindrical sheathing member 38 is a fluororesin-based tube and the cover 110 of the curvature detection optical fiber 103*a* is also formed of a similar fluororesin, the cylindrical sheathing member 38 and curvature detection optical fiber 103*a* may be fixed by fusion.

[Modification of Fixation of the Rear End of Cylindrical Sheathing Member 38]

In the above-described embodiment, both of the distal end portion and rear end portion of the cylindrical sheathing member 38 are fixed. For example, in one modification, the distal end portion or rear end portion of the cylindrical sheathing member 38 may be provided with a tension applying mechanism.

Figure 11:
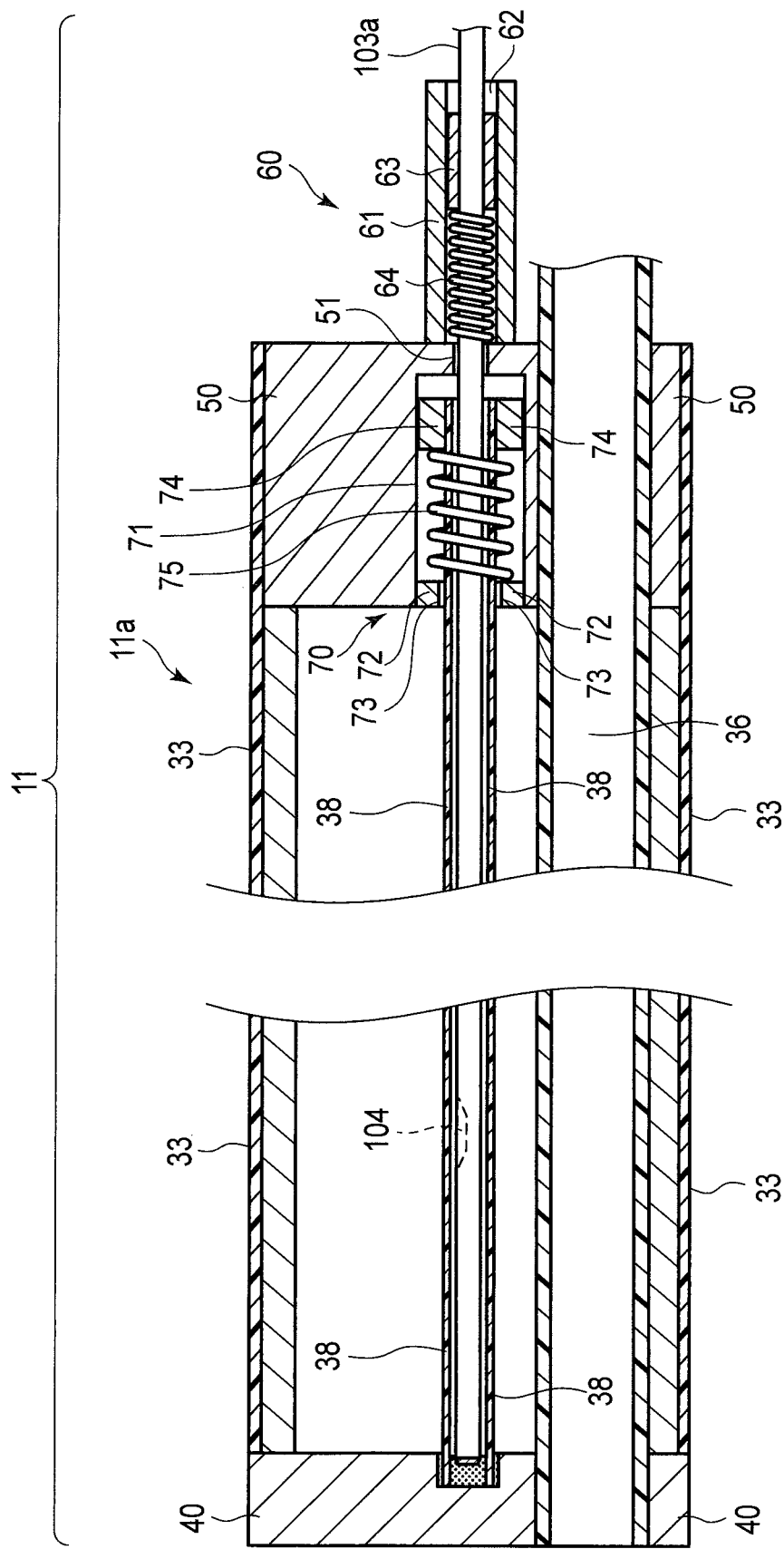
FIG. 11 is a cross-sectional view corresponding to FIG. 5, FIG. 11 schematically showing the entire configuration of a bendable section of an insertion section relating to a modification in which a tension applying mechanism is provided in a rear end portion of a cylindrical sheathing member.

FIG. 11 is a cross-sectional view corresponding to FIG. 5, FIG. 11 schematically showing the entire configuration of a bendable section 11a of an insertion section 11 relating to a modification in which a tension applying mechanism 70 is provided in a rear end portion of a cylindrical sheathing member 38. As illustrated in FIG. 11, the bendable section rear-end member 50 includes the tension applying mechanism 70 to apply tension to the cylindrical sheathing member 38 in the longitudinal direction thereof. The bendable section rear-end member 50 includes a guide hole 71 in place of the recess portion 52. The tension applying mechanism 70 includes a stopper 72 fixed to an opening end of the guide hole 71, and a movable member 74 and an elastic member 75, which are contained in the guide hole 71. The stopper 72 has a through hole 73, and the cylindrical sheathing member 38 passes through the through hole 73 of the stopper 72 and extends up to an intermediate portion of the guide hole 71. The movable member 74 is fixed to a rear end portion of the cylindrical sheathing member 38. The elastic member 75 may be, for example, a coil spring, and has a greater diameter than the through hole 73. The elastic member 75 is disposed in a compressed state between the stopper 72 and movable member 74 in the guide hole 71. Thereby, the movable member 74 is pushed by the restoring force of the elastic member 75 toward the rear end of the insertion section 11, i.e. toward the control section 12. As a result, the cylindrical sheathing member 38 extends without slacking.

The relationship of engagement between the guide hole 71 and movable member 74 of the tension applying mechanism 70 is the same as the relationship of engagement between the guide hole 62 and movable member 63 of the tension applying mechanism 60. Specifically, the guide hole 71 has a rectangular cross section perpendicular to the axis thereof. The movable member 74 has such a rectangular prismatic outer shape as to just fit in the guide hole 71. Thus, the movable member 74 can axially move in the guide hole 71, but cannot rotate about the axis. Thereby, the cylindrical sheathing member 38 is prevented from twisting. Specifically, the movable member 74 and guide hole 71 cooperate to constitute a twist prevent mechanism to prevent the cylindrical sheathing member 38 from twisting about the longitudinal axis thereof.

Second Embodiment

Figure 14:
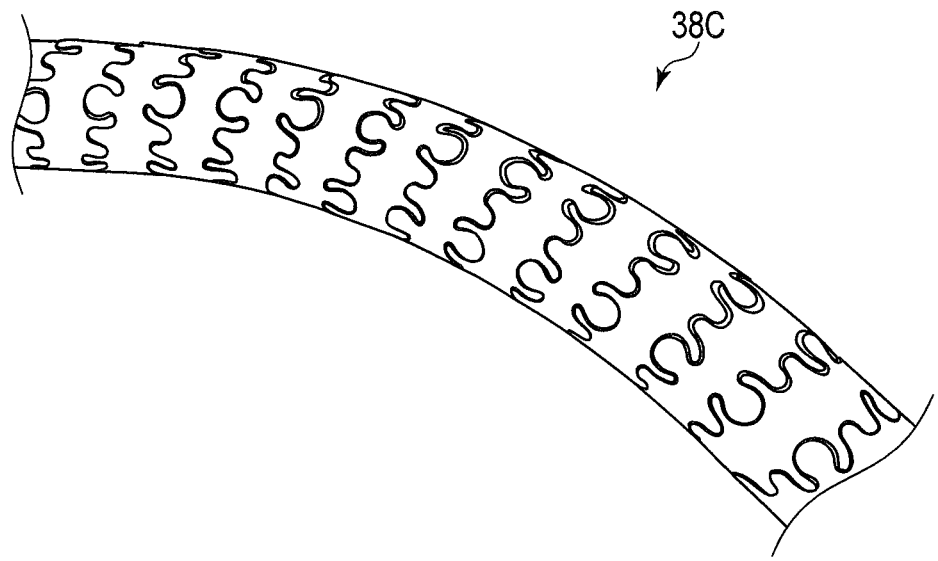
FIG. 14 shows still another cylindrical sheathing member in the second embodiment.

The present embodiment is directed to some cylindrical sheathing members that are applicable in place of the cylindrical sheathing member 38 of the first embodiment. A cylindrical sheathing member 38A shown in FIG. 12 is formed with many openings, which are formed in order to improve the flexibility of the cylindrical sheathing member 38A. A cylindrical wall of the cylindrical sheathing member 38A is formed in a mesh shape. A cylindrical sheathing member 38B shown in FIG. 13 is formed with a helical slit, which is formed in order to improve the flexibility of the cylindrical sheathing member 38B. A cylindrical sheathing member 38C shown in FIG. 14 is formed with a wavy slit, which is formed in order to improve the flexibility of the cylindrical sheathing member 38C.

The cylindrical sheathing member 38A, 38B, 38C may be formed of a metallic tube, and the openings and slits may be formed by laser processing. Since the openings or slits are formed in the cylindrical sheathing member 38A, 38B, 38C, the flexibility is improved. Since the flexibility is improved by providing the openings or slits, a member with high flexural rigidity, for example, a metallic pipe with a large wall thickness, may be used as the base material of the cylindrical sheathing member 38A, 38B, 38C. Specifically, the range of choices of the usable material for the cylindrical sheathing member 38A, 38B, 38C increases.

Since the cylindrical sheathing member 38A, 38B, 38C of this embodiment may be applied in place of the cylindrical sheathing member 38 of the first embodiment, the degree of freedom of design of the shape measuring cylindrical flexible body apparatus is improved.

Third Embodiment

Figure 15:
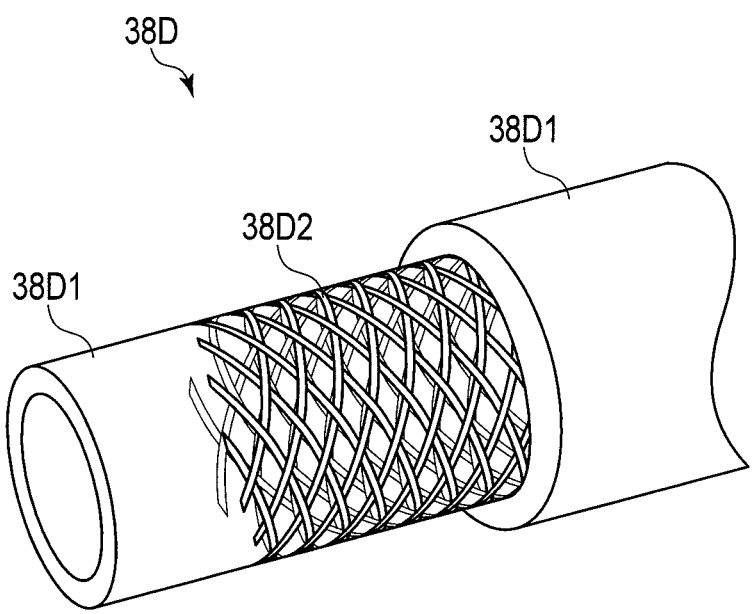
FIG. 15 shows a cylindrical sheathing member in a third embodiment.
Figure 16:
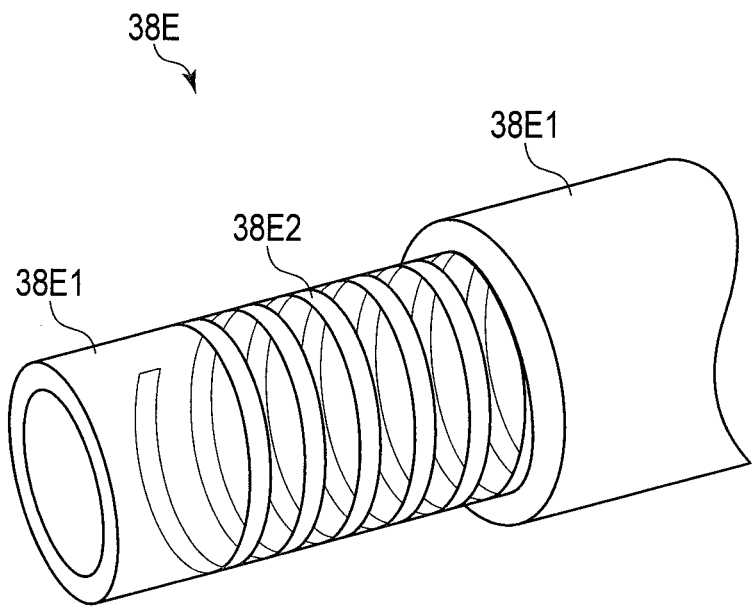
FIG. 16 shows another cylindrical sheathing member in the third embodiment.

The present embodiment is directed to some cylindrical sheathing members that are applicable in place of the cylindrical sheathing member 38 of the first embodiment. A cylindrical sheathing member 38D shown in FIG. 15 has a resin tube 38D1, and a braid 38D2 that is a reinforcement member buried within the resin tube 38D1. A cylindrical sheathing member 38E shown in FIG. 16 has a resin tube 38E1, and a coil 38E2 that is a reinforcement member buried within the resin tube 38E1. The braid 38D2 and coil 38E2 may be made of, for example, a metal. The cylindrical sheathing members 38D and 38E may be formed of a material of polyimide or polyamide by integral molding with the braid 38D2 and coil 38E2, respectively.

Since the cylindrical sheathing members 38D and 38E has the braid 38D2 and coil 38E2 that are buried in the insides of the cylindrical sheathing members 38D and 38E, respectively, the torsional rigidity of the cylindrical sheathing member 38D, 38E is improved, compared to a cylindrical sheathing member composed of a resin tube without a reinforcement member. Thus, a deformation in radial cross section of the cylindrical sheathing member 38D, 38E at a time of bending of the bendable section 11a of the insertion section 11 is decreased. Moreover, the occurrence of a twist, which occurs when some other built-in component or elongated hollow member 33 comes in contact with the cylindrical sheathing member 38D, 38E, can be reduced.

The precision and reliability of the shape measuring cylindrical flexible body apparatus are improved by the cylindrical sheathing member 38D, 38E of this embodiment being applied in place of the resin-made cylindrical sheathing member 38 of the first embodiment.

Fourth Embodiment

Figure 17:
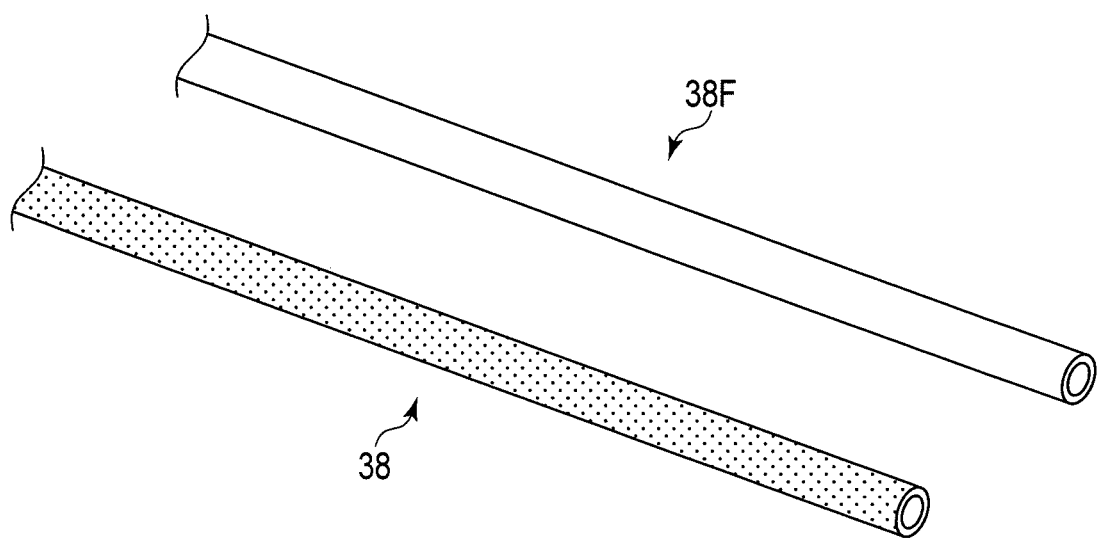
FIG. 17 shows a cylindrical sheathing member in a fourth embodiment.

The present embodiment is directed to a cylindrical sheathing member that is applicable in place of the cylindrical sheathing member 38 of the first embodiment. A cylindrical sheathing member 38F shown in FIG. 17 is composed by applying a smoothing process by polishing to an inner peripheral surface or an outer peripheral surface or both the inner and outer peripheral surfaces of the cylindrical sheathing member 38 of the first embodiment. Specifically, the cylindrical sheathing member 38F has the inner peripheral surface and/or outer peripheral surface that have been subjected to the smoothing process. By the smoothing process, the frictional resistance of the inner peripheral surface and/or outer peripheral surface of the cylindrical sheathing member 38F is decreased. The inner peripheral surface and/or outer peripheral surface, which have been subjected to the smoothing process, may have a surface roughness that satisfies a center line average height Ra of at least Ra≤6.2 µm, preferably Ra≤0.8 µm.

By the inner peripheral surface being polished, compared to the cylindrical sheathing member 38, the friction between the cylindrical sheathing member 38F and curvature detection optical fiber 103a is decreased, and the reliability of the bend detection sensor 101 is improved. By the outer peripheral surface being polished, compared to the cylindrical sheathing member 38, the friction between some other built-in component or elongated hollow member 33 and the cylindrical sheathing member 38F is decreased, the cylindrical sheathing member 38F does not easily receive a torque, and the curvature detection optical fiber 103a does not easily twist.

The precision and reliability of the shape measuring cylindrical flexible body apparatus are improved by the cylindrical sheathing member 38F of this embodiment being applied in place of the cylindrical sheathing member 38 of the first embodiment.

Fifth Embodiment

The present embodiment is directed to some cylindrical sheathing members that are applicable in place of the cylindrical sheathing member 38 of the first embodiment. A cylindrical sheathing member 38G shown in FIG. 18 is configured such that many circular dimples 38G1, or small circular recesses, are discretely formed on an outer peripheral surface of the cylindrical sheathing member 38G. A cylindrical sheathing member 38H shown in FIG. 19 is configured such that many hexagonal dimples 38H1, or small circular recesses, are formed in a mutually neighboring manner on an outer peripheral surface of the cylindrical sheathing member 38H. By the formation of the many dimples, the contact area between the cylindrical sheathing member 38G, 38H and the outside is decreased. Specifically, the cylindrical sheathing member 38G, 38H has a processed portion that has been processed to decrease the contact area with the outside. The dimples may be formed by, for example, a shot-peening process or a press process.

Compared to the cylindrical sheathing member 38, since the cylindrical sheathing member 38G, 38H has a decreased contact area with the outside, the cylindrical sheathing member 38G, 38H does not easily receive a torque and the curvature detection optical fiber 103a does not easily twist, when the cylindrical sheathing member 38G, 38H comes in contact with some other built-in component or elongated hollow member 33.

The precision and reliability of the shape measuring cylindrical flexible body apparatus are improved by the cylindrical sheathing member 38G, 38H of this embodiment being applied in place of the cylindrical sheathing member 38 of the first embodiment.

Sixth Embodiment

The present embodiment is directed to a cylindrical sheathing member that is applicable in place of the cylindrical sheathing member 38 of the first embodiment. A cylindrical sheathing member 38I shown in FIG. 20 is composed of a bellows cylinder. Specifically, the cylindrical sheathing member 38I has many circumferential grooves, which are arranged along the longitudinal axis thereof. Instead of being composed of the bellows cylinder, the cylindrical sheathing member 38I may be composed of a helical groove cylinder having a single helical groove. Thereby, the contact area of the cylindrical sheathing member 38I with the outside is decreased. Specifically, the cylindrical sheathing member 38I has a processed portion that has been processed to decrease the contact area with the outside. In particular, in usual cases, a built-in component in the insertion section 11 has an elongated cylindrical outer shape. Thus, the contact between the cylindrical sheathing member 38I and the built-in component of the insertion section 11 is substantially a point contact. The bellows cylinder or helical groove cylinder may be formed by, for example, die-processing. In addition, the flexibility of the bellows cylinder or helical groove cylinder is improved, compared to the circular cylinder before being processed.

Compared to the cylindrical sheathing member 38, since the cylindrical sheathing member 38I has a decreased contact area with the outside, the cylindrical sheathing member 38I does not easily receive a torque and the curvature detection optical fiber 103a does not easily twist, when the cylindrical sheathing member 38I comes in contact with some other built-in component or elongated hollow member 33.

The precision and reliability of the shape measuring cylindrical flexible body apparatus are improved by the cylindrical sheathing member 38I of this embodiment being applied in place of the cylindrical sheathing member 38 of the first embodiment.

Seventh Embodiment

The present embodiment is directed to a cylindrical sheathing member that is applicable in place of the cylindrical sheathing member 38 of the first embodiment. A cylindrical sheathing member 38J shown in FIG. 21 is composed of a metal tube 38J1, a resin coat 38J2 formed on an inner peripheral surface of the metal tube 38J1, and a resin coat 38J3 formed on an outer peripheral surface of the metal tube 38J1. Each of the resin coats 38J2 and 38J3 has a friction coefficient that is lower than the friction coefficient of the metal tube 38J1. The resin coat 38J2, 38J3 may be formed of, for example, PTFE, ETFE, or other fluororesin. Since the resin coats 38J2 and 38J3 are formed on the inner peripheral surface and outer peripheral surface of the metal tube 38J1, the frictional resistances of the inner peripheral surface and outer peripheral surface of the cylindrical sheathing member 38J are decreased, compared to the case in which the cylindrical sheathing member 38J is composed of the metal tube 38J1 itself. Depending on cases, one of the resin coats 38J2 and 38J3 may be omitted.

By the formation of the resin coat 38J2, the friction between the cylindrical sheathing member 38J and curvature detection optical fiber 103a is decreased, and the reliability of the bend detection sensor 101 is improved, compared to the case in which the cylindrical sheathing member 38J is composed of the metal tube 38J1 itself. By the formation of the resin coat 38J3, the friction between some other built-in component or elongated hollow member 33 and the cylindrical sheathing member 38J is decreased, the cylindrical sheathing member 38J does not easily receive a torque, and the curvature detection optical fiber 103a does not easily twist, compared to the case in which the cylindrical sheathing member 38J is composed of the metal tube 38J1 itself.

The precision and reliability of the shape measuring cylindrical flexible body apparatus are improved by the cylindrical sheathing member 38J of this embodiment being applied in place of the metallic cylindrical sheathing member 38 of the first embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A shape measuring cylindrical flexible body apparatus comprising:
   a cylindrical flexible body having a distal end and a proximal end;
   a bend detection sensor comprising:
      a light source configured to radiate detection light,
      an optical fiber extending along a longitudinal direction of the cylindrical flexible body, the optical fiber being configured to guide the detection light radiated from the light source,
      at least one detection target provided in the optical fiber configured to vary characteristics of the detection light in accordance with a curvature of the optical fiber, and
      a light detection sensor configured to detect the detection light guided through the optical fiber;
   a controller comprising hardware, the controller being configured to calculate a bend shape of the cylindrical flexible body, based on the variation of the characteristics of the detection light detected by the light detection sensor;
   a cylindrical sheathing member disposed in an inside of the cylindrical flexible body, the cylindrical sheathing member being a cylindrical member to sheathe at least a part of the optical fiber; and
   a hard distal member provided at the distal end of the cylindrical flexible body, the hard distal member being configured to hold a distal end of the cylindrical sheathing member;
   wherein the cylindrical sheathing member has a flexibility that is equal to or greater than a flexibility of the optical fiber.

2. The shape measuring cylindrical flexible body apparatus of claim 1, wherein the cylindrical sheathing member has a torsional rigidity that is higher than a torsional rigidity of the optical fiber.

3. The shape measuring cylindrical flexible body apparatus of claim 2, wherein the cylindrical sheathing member includes a resin tube, and a reinforcement member buried within the resin tube.

4. The shape measuring cylindrical flexible body apparatus of claim 3, wherein the reinforcement member is composed of at least one of a braid and a coil.

5. The shape measuring cylindrical flexible body apparatus of claim 2, wherein the cylindrical sheathing member has a slit formed to improve the flexibility of the cylindrical sheathing member.

6. The shape measuring cylindrical flexible body apparatus of claim 2, wherein the cylindrical sheathing member has a processed portion processed to decrease a contact area with an outside.

7. The shape measuring cylindrical flexible body apparatus of claim 2, wherein the cylindrical sheathing member has an outer peripheral surface subjected to a smoothing process.

8. The shape measuring cylindrical flexible body apparatus of claim 2, wherein the cylindrical sheathing member is composed of a metal tube and a resin coat formed on at least one of an inner peripheral surface and an outer peripheral surface of the metal tube, the resin coat having a friction coefficient that is lower than a friction coefficient of the metal tube.

9. The shape measuring cylindrical flexible body apparatus of claim 2, further comprising a lubricant lying between the cylindrical sheathing member and the optical fiber.

10. The shape measuring cylindrical flexible body apparatus of claim 1, further comprising a biasing spring configured to apply tension to the cylindrical sheathing member in a longitudinal direction of the optical fiber.

11. The shape measuring cylindrical flexible body apparatus of claim 10, further comprising a sliding surface arranged on the optical fiber, the sliding surface being configured to move along the longitudinal axis of the optical fiber and to prevent the cylindrical sheathing member from twisting about the longitudinal axis of the optical fiber.

12. The shape measuring cylindrical flexible body apparatus of claim 1, wherein the shape measuring cylindrical flexible body apparatus is an endoscope apparatus, and the cylindrical flexible body is an insertion section of the endoscope apparatus.

13. A shape measuring cylindrical flexible body apparatus of claim 1, further comprising:
   a cylindrical flexible body having a distal end and a proximal end;
   a bend detection sensor comprising:
      a light source configured to radiate detection light,
      an optical fiber extending along a longitudinal direction of the cylindrical flexible body, the optical fiber being configured to guide the detection light radiated from the light source,
      at least one detection target provided in the optical fiber configured to vary characteristics of the detection light in accordance with a curvature of the optical fiber, and
      a light detection sensor configured to detect the detection light guided through the optical fiber;
   a controller comprising hardware, the controller being configured to calculate a bend shape of the cylindrical flexible body, based on the variation of the characteristics of the detection light detected by the light detection sensor;
   a cylindrical sheathing member disposed in an inside of the cylindrical flexible body, the cylindrical sheathing member being a cylindrical member to sheathe at least a part of the optical fiber; and
   a hard distal member provided at the distal end of the cylindrical flexible body, the hard distal member being configured to hold a distal end of the cylindrical sheathing member; and
   a biasing spring configured to apply tension to the optical fiber in a longitudinal direction of the optical fiber.

14. The shape measuring cylindrical flexible body apparatus of claim 13, further comprising a sliding surface arranged on the optical fiber, the sliding surface being configured to move along the longitudinal axis of the optical fiber and to prevent the optical fiber from twisting about the longitudinal axis of the optical fiber.

* * * * *